US010821108B2

(12) United States Patent
Furuta et al.

(10) Patent No.: US 10,821,108 B2
(45) Date of Patent: Nov. 3, 2020

(54) PHARMACEUTICAL COMPOSITION CONTAINING 2-{4-[N-(5,6-DIPHENYLPYRAZIN-2-YL)-N-ISOPROPYLAMINO]BUTYLOXY}-N-(METHYLSULFONYL)ACETAMIDE

(71) Applicant: NIPPON SHINYAKU CO., LTD., Kyoto-shi, Kyoto (JP)

(72) Inventors: Shouji Furuta, Kyoto (JP); Hironori Mukai, Kyoto (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 0 days.

(21) Appl. No.: 15/777,711

(22) PCT Filed: Dec. 1, 2016

(86) PCT No.: PCT/JP2016/085822
§ 371 (c)(1),
(2) Date: May 21, 2018

(87) PCT Pub. No.: WO2017/098998
PCT Pub. Date: Jun. 15, 2017

(65) Prior Publication Data
US 2018/0333413 A1 Nov. 22, 2018

(30) Foreign Application Priority Data
Dec. 2, 2015 (JP) ................. 2015-236034

(51) Int. Cl.
*A61K 31/4965* (2006.01)
*A61K 9/20* (2006.01)
*A61P 11/00* (2006.01)
*A61K 9/16* (2006.01)
*A61P 11/06* (2006.01)
*A61P 9/10* (2006.01)
*A61P 7/02* (2006.01)
*A61P 13/12* (2006.01)
*A61P 9/12* (2006.01)
*A61K 47/38* (2006.01)
*A61K 31/047* (2006.01)

(52) U.S. Cl.
CPC ........ *A61K 31/4965* (2013.01); *A61K 9/1611* (2013.01); *A61K 9/1623* (2013.01); *A61K 9/1652* (2013.01); *A61K 9/2013* (2013.01); *A61K 9/2018* (2013.01); *A61K 9/2054* (2013.01); *A61K 9/2059* (2013.01); *A61K 47/38* (2013.01); *A61P 7/02* (2018.01); *A61P 9/10* (2018.01); *A61P 9/12* (2018.01); *A61P 11/00* (2018.01); *A61P 11/06* (2018.01); *A61P 13/12* (2018.01); *A61K 31/047* (2013.01); *A61K 2300/00* (2013.01)

(58) Field of Classification Search
None
See application file for complete search history.

(56) References Cited

U.S. PATENT DOCUMENTS

| 8,394,793 | B2* | 3/2013 | Kyoi ............... C07D 241/20 514/231.2 |
| 9,173,842 | B2 | 11/2015 | Paillard et al. |
| 2001/0001106 | A1 | 5/2001 | Yoshinari et al. |
| 2004/0102436 | A1* | 5/2004 | Asaki ............. A61K 31/4418 514/217.05 |
| 2010/0196468 | A1 | 8/2010 | Paillard et al. |
| 2011/0015211 | A1 | 1/2011 | Murakami et al. |
| 2011/0105518 | A1 | 5/2011 | Kuwano |
| 2011/0118254 | A1 | 5/2011 | Kyoi |
| 2012/0101276 | A1 | 4/2012 | Itou et al. |
| 2014/0148469 | A1 | 5/2014 | Itou |
| 2015/0272874 | A1 | 10/2015 | Sawa et al. |

FOREIGN PATENT DOCUMENTS

| CN | 103690496 A | 4/2014 |
| CN | 103690496 B | 4/2015 |
| EP | 1 400 518 A1 | 3/2004 |
| EP | 1 400 518 B1 | 1/2007 |
| EP | 2 289 518 A1 | 3/2011 |
| EP | 2 447 254 A1 | 5/2012 |
| EP | 2 289 518 B1 | 11/2016 |
| JP | H10-036291 A | 2/1998 |
| JP | 3145431 B2 | 3/2001 |
| RU | 2 462 248 C2 | 9/2012 |
| WO | 2001/089520 A2 | 11/2001 |
| WO | 2002/088084 A1 | 11/2002 |
| WO | 2009/107736 A1 | 9/2009 |
| WO | 2009/154246 A1 | 12/2009 |
| WO | 2009/157396 A1 | 12/2009 |
| WO | 2009/157397 A1 | 12/2009 |
| WO | 2009/157398 A1 | 12/2009 |
| WO | 2010/150865 A1 | 12/2010 |

(Continued)

OTHER PUBLICATIONS

Airaksinen (Airaksinen, S., et al., Role of Water in the Physical Stability of Solid Dosage Formulations, J. Pharm. Sci. 94 (Oct. 2005) pp. 2147-2165) (Year: 2005).*
Airaksinen, S., et al., Role of Water in the Physical Stability of Solid Dosage Formulations, J. Pharm. Sci. 94 (Oct. 2005) pp. 2147-2165. (Year: 2005).*
English Language Translation of CN 103690496 A (Year: 2014).*
English Language Translation of CN 103690496 B (Year: 2015).*
English Language Translation of JP 3145431 B2 (Year: 2001).*
Sari Airaksinen et al. "Role of Water in the Physical Stability of Solid Dosage Formulations," Journal of Pharmaceutical Sciences, vol. 94, No. 10, pp. 2147-2165 (Oct. 2005).

(Continued)

*Primary Examiner* — Dominic Lazaro

(57) ABSTRACT

A stabilized solid preparation containing 2-{4-[N-(5,6-diphenylpyrazin-2-yl)-N-isopropylamino]butyloxy}-N-(methylsulfonyl)acetamide is provided, namely, a solid preparation containing 2-{4-[N-(5,6-diphenylpyrazin-2-yl)-N-isopropylamino]butyloxy}-N-(methylsulfonyl)acetamide and D-mannitol having a specific surface area of 1.0 m²/g or less.

26 Claims, 2 Drawing Sheets

(56) References Cited

FOREIGN PATENT DOCUMENTS

WO    2014/069401 A1    5/2014

OTHER PUBLICATIONS

Tatsuya Atsumi et al., "Improvement of skin temperature of fingers by beraprost sodium in patients with Raynaud's phenomenon," Japanese Journal of Clinical Immunology, vol. 16, Issue 5, pp. 409-414 (1993).

David B. Badesch et al., "Longterm Survival Among Patients with Scleroderma-associated Pulmonary Arterial Hypertension Treated with Intravenous Epoprostenol," The Journal of Rheumatology, vol. 36 (10), pp. 2244-2249 (Oct. 2009).

G. Bergman et al., "Prostacyclin: Haemodynamic and Metabolic Effects in Patients With Coronary Artery Disease," The Lancet, vol. 317, Issue 8220, pp. 569-572 (Mar. 14, 1981) Elsevier B.V.

Yan Chen et al., "Protective effect of beraprost sodium, a stable prostacyclin analog, in the development of cigarette smoke extract-induced emphysema," American Journal of Physiology Lung Cellular and Molecular Physiology, vol. 296, pp. L648-L656 (2009) The American Physiological Society.

P. Henriksson et al., "Prostacyclin infusion in patients with acute myocardial infarction," British Heart Journal, vol. 53, pp. 173-179 (1985).

Tetsuya Hirano et al., "Effect of Beraprost Sodium (TRK-100) on Erythrocyte Deformability, Blood Viscosity and Thrombus Formation in Rats," Japanese Journal of Thrombosis and Hemostasis, vol. 1, No. 2, pp. 94-105 (1990).

Marco Idzko et al., "Inhaled iloprost suppresses the cardinal features of asthma via inhibition of airway dendritic cell function," The Journal of Clinical Investigation, vol. 117, No. 2, pp. 464-472 (Feb. 2007) American Society for Clinical Investigation.

T. Matsumoto et al., "The efficacy of Oral Beraprost Sodium, a prostaglandin I2 analogue, for treating intermittent claudication in patients with arteriosclerosis obliterans," International Angiology, vol. 29, Supplement 1 to No. 2, pp. 49-54 (Apr. 2010) Edizioni Minerva Medica.

Shintaro Nishio and Hajimu Kurumatani, "Pharmacological and clinical properties of beraprost sodium, orally active prostacyclin analogue," Folia Pharmacologica Japonica (Nihon Yakurigaku Zasshi), vol. 117, pp. 123-130 (2001).

Fumiaki Ono et al., "Effect of Orally Active Prostacyclin Analogue on Survival in Patients With Chronic Thromboembolic Pulmonary Hypertension Without Major Vessel Obstruction," Chest, vol. 123, Issue 5, pp. 1583-1588 (May 2003).

Olivier Sitbon et al., "Selexipag for the Treatment of Pulmonary Arterial Hypertension," The New England Journal of Medicine, vol. 373, No. 26, pp. 2522-2533 (Dec. 24, 2015) Massachusetts Medical Society.

Teruhiko Umetsu et al., "Antithrombotic Effect of TRK-100, a Novel, Stable PGI2 Analogue," The Japanese Journal of Pharmacology, vol. 43, pp. 81-90 (1987).

Masateru Yamada et al., "Amelioration by beraprost sodium, a prostacyclin analogue, of established renal dysfunction in rat glomerulonephritis model," European Journal of Pharmacology, vol. 449, Issue 1-2, pp. 167-176 (2002) Elsevier Science B.V.

Hao Yin et al., "Prostaglandin I2 and E2 Mediate the Protective Effects of Cyclooxygenase-2 in a Mouse Model of Immune-Mediated Liver Injury," Hepatology, vol. 45, No. 1, pp. 159-169 (Jan. 2007).

International Searching Authority, "Written Opinion," issued in International Application No. PCT/JP2016/085822, of which U.S. Appl. No. 15/777,711 is a U.S. national phase entry, dated Dec. 27, 2016, 6 pages.

"Amorphous Selexipag Formulations", Research Disclosure, Kenneth Mason Publications, Hampshire, UK, GB, vol. 618, No. 27, Oct. 1, 2015 (Oct. 1, 2015), p. 2, XP007144400, ISSN: 0374-4353.

Daniela Baldoni et al., "Bioequivalence of different dose-strength tablets of selexipag, a selective prostacyclin receptor agonist, in a multiple-dose up-titration study", International Journal of Clinical Pharmacology and Therapeutics, vol. 53, No. 9, Sep. 1, 2015 (Sep. 1, 2015), pp. 788-798, XP009511878, Dustri-Verlag, Deisenhofen-Muenchen, DE ISSN: 0946-1965, DOI: 10.5414/CP202318.

Sudharshan Hariharan and Luning Zhuang, "Clinical Pharmacology and Biopharmaceutics Review(s)—Application No. 207947Orig1s000", FDA-Center for Drug Evaluation and Research, Dec. 22, 2014 (Dec. 22, 2014), pp. 1-31, XP002789805, retrieved from the Internet: URL:https://www.accessdata.fda.gov/drugsatfda_docs/nda/2015/207947Orig1s000ClinPharmR.pdf.

Rowe et al., "Mannitol", Handbook of Pharmaceutical Excipients, 7th Edn., Pharmaceutical Press, Jan. 1, 2012 (Jan. 1, 2012), pp. 479-482, XP002789781, retrieved from the Internet: URL:https://www.pharmpress.com/files/docs/Excipients7e_samplemonos(1).pdf.

European Patent Office, "Extended European Search Report", issued in European Patent Application No. 16 872 896.2, which is a European counterpart of U.S. Appl. No. 15/777,711, dated Apr. 12, 2019, 10 pages.

Opposition paper filed on behalf of Asociacion de Laboratorios Farmaceuticos (ALAFAR) against an Ecuadorean counterpart of U.S. Appl. No. 15/777,711, bearing a date of Feb. 8, 2019, with 14 pages of original document followed by 14 pages of English translation thereof.

Opposition paper filed on behalf of Laboratorio Granco Colombiano Lafrancol S.A.S. against a Colombian counterpart of U.S. Appl. No. 15/777,711, bearing a date of Nov. 26, 2018, with 17 pages of original document followed by 20 pages of English translation thereof.

Office Action issued by Republic of Colombia Superintendency of Industry and Commerce in a Colombian counterpart of U.S. Appl. No. 15/777,711, dated Jul. 5, 2019, with 7 pages of original document followed by 10 pages of English translation thereof.

Office Action issued by National Institute of Industrial Property of Chile (INAPI) in a Chilean counterpart of U.S. Appl. No. 15/777,711, dated Apr. 15, 2019, with 8 pages of original document followed by 4 pages of English translation thereof.

Office Action issued by National Institute of Industrial Property of Chile (INAPI) in a Chilean counterpart of U.S. Appl. No. 15/777,711, dated Aug. 13, 2019, with 7 pages of original document followed by 4 pages of English translation thereof.

Restriction Requirement issued by United States Patent and Trademark Office in U.S. Appl. No. 16/044,821, which is a child application of U.S. Appl. No. 15/777,711, dated Sep. 14, 2018, 5 pages.

Non-Final Office Action issued by United States Patent and Trademark Office in U.S. Appl. No. 16/044,821, which is a child application of U.S. Appl. No. 15/777,711, dated Nov. 30, 2018, 23 pages.

Final Office Action issued by United States Patent and Trademark Office in U.S. Appl. No. 16/044,821, which is a child application of U.S. Appl. No. 15/777,711, dated May 29, 2019, 22 pages.

United States Patent and Trademark Office, "Non-Final Office Action", issued in U.S. Appl. No. 16/044,821, dated Nov. 18, 2019, 23 pages.

United States Patent and Trademark Office, "Non-Final Office Action", issued in U.S. Appl. No. 16/044,821, dated Jan. 6, 2020, 10 pages.

Intellectual Property India, Government of India, "Examination Report", issued in Indian Patent Application No. 201847023536, which is a counterpart of U.S. Appl. No. 15/777,711, dated Feb. 21, 2020, 6 pages.

Russian Federation Federal Service for Intellectual Property (ROSPAT), Ministry of Economic Development of the Russian Federation, "Office Action", issued in Russian Patent Application No. 2018123304/04(036931), which is a counterpart of U.S. Appl. No. 15/777,711, dated Mar. 31, 2020, 13 pages (7 pages of original Office Action, and 6 pages of English translation of Office Action).

United States Patent and Trademark Office, "Non-Final Office Action", issued in U.S. Appl. No. 16/044,821, dated May 15, 2020, 17 pages.

ICH Harmonised Tripartite Guideline, "Stability Testing of New Drug Substances and Products Q1A(R2)", International Conference

(56) References Cited

OTHER PUBLICATIONS on Harmonisation of Technical Requirements for Registration of Pharmaceuticals for Human Use, Current Step 4 version, dated Feb. 6, 2003, 24 pages.

Superintendence of Industry and Commerce, Direction of New Creations, "Office Action No. 1153", issued in Colombian Patent Application No. NC2018/0006834, which is a counterpart of U.S. Appl. No. 15/777,711, dated Jan. 22, 2020, 19 pages (7 pages of original Office Action, and 12 pages of English translation of Office Action).

Japan Patent Office, "Notice of Reasons for Refusal", issued in Japanese Patent Application No. 2017-555036, which is a counterpart of U.S. Appl. No. 15/777,711, dated May 19, 2020, 10 pages (3 pages of original Office Action, and 7 pages of English translation of Office Action).

Taiwan Intellectual Property Office, "Office Action of the Intellectual Property Office", issued in Taiwanese Patent Application No. 105139756, which is a counterpart of U.S. Appl. No. 15/777,711, dated Apr. 30, 2020, 10 pages (6 pages of original Office Action, and 4 pages of English translation of Office Action).

Naoki Wakiyama, "Stability and Shelf Life of Pharmaceutical Products", Materials Life, vol. 3, No. 2, pp. 104-109 (Apr. 1991) (6 pages of original monograph, and 11 pages of English translation of monograph).

Russian Federation Federal Service for Intellectual Property (ROSPAT), Ministry of Economic Development of the Russian Federation, "Official Action", issued in Russian Patent Application No. 2018123304/04(036931), which is a counterpart of U.S. Appl. No. 15/777,711, dated Jun. 29, 2020, 8 pages (5 pages of original Official Action, and 3 pages of English translation of Official Action).

European Patent Office, "Communication," issued in European Patent Application No. 16 872 896.2, which is a European counterpart of U.S. Appl. No. 15/777,711, with an issuance date of Jul. 8, 2020, 4 pages.

China National Intellectual Property Administration, "First Office Action", issued in Chinese Patent Application No. 201680068849.X, which is a counterpart to U.S. Appl. No. 15/777,711, dated Jun. 30, 2020, 12 pages (5 pages of original Chinese Office Action, and 7 pages of English translation of Office Action).

Raymond C. Rowe, Paul J. Sheskey and Marian E. Quinn, "Mannitol," from Handbook of Pharmaceutical Excipients, Sixth Edition, pp. 424-428 (2006), Pharmaceutical Press.

Taiwan Intellectual Property Office, "Decision of the Intellectual Property Office", issued in Taiwanese Patent Application No. 105139756, which is a counterpart of U.S. Appl. No. 15/777,711, dated Aug. 26, 2020, 8 pages (5 pages of original Decision, and 3 pages of English translation of Decision).

\* cited by examiner

PHARMACEUTICAL COMPOSITION CONTAINING 2-{4-[N-(5,6-DIPHENYLPYRAZIN-2-YL)-N-ISOPROPYLAMINO]BUTYLOXY}-N-(METHYLSULFONYL)ACETAMIDE

CROSS REFERENCE TO RELATED APPLICATIONS

This patent application is a U.S. national stage application under 35 U.S.C. § 371 of International Patent Application No. PCT/JP2016/085822 filed on Dec. 1, 2016, which claims the benefit of foreign priority to Japanese Patent Application No. JP 2015-236034 filed on Dec. 2, 2015. The International Application was published in Japanese on Jun. 15, 2017, as International Publication No. WO 2017/098998 A1 under PCT Article 21(2).

TECHNICAL FIELD

The present invention relates to a stabilized solid preparation containing 2-{4-[N-(5,6-diphenylpyrazin-2-yl)-N-isopropylamino]butyloxy}-N-(methylsulfonyl)acetamide (hereinafter referred to as "Compound (I)").

BACKGROUND ART

It is known that Compound (I) represented by the following structural formula has an excellent prostaglandin $I_2$ (also referred to as $PGI_2$) receptor agonistic activity and shows various medicinal effects such as a platelet aggregation inhibitory effect, a vasodilating effect, a bronchial smooth muscle dilating effect, a lipid deposition inhibitory effect, and a leukocyte activation inhibitory effect (PTL 1).

[Chem. 1]

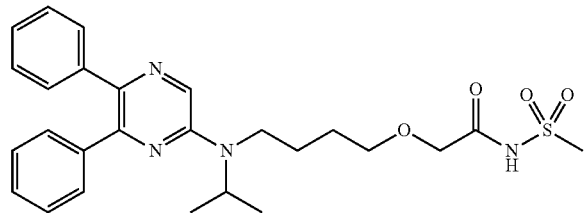

(I)

In general, as diluents for a solid preparation, lactose, cornstarch, crystalline cellulose, and sugar alcohols such as D-mannitol are used for diluting an active ingredient. In the process for studying the formulation of a solid preparation containing Compound (I), it was found that Compound (I) itself is stable to temperature and humidity; however, depending on the type of D-mannitol, the decomposition of Compound (I) in the solid preparation proceeds, and the content thereof decreases.

CITATION LIST

Patent Literature

[PTL 1] WO 2002/088084
[PTL 2] WO 2009/157396
[PTL 3] WO 2009/107736
[PTL 4] WO 2009/154246
[PTL 5] WO 2009/157397
[PTL 6] WO 2009/157398
[PTL 7] WO 2009/154246
[PTL 8] WO 2009/157397

Non Patent Literature

[NPL 1] Hepatology, 2007, Vol. 45, No. 1, pp. 159-169.
[NPL 2] Folia Pharmacologica Japonica, Vol. 117, No. 2, pp. 123-130, 2001, Abstract.
[NPL 3] International Angiology, 29, Suppl. 1 to No. 2, pp. 49-54, 2010.
[NPL 4] Jpn. J. Clin. Immunol., 16(5), 409-414, 1993.
[NPL 5] Jpn. J. Thromb. Hemost., 1:2, pp. 94-105, 1990, Abstract.
[NPL 6] J. Rheumatol., 2009, 36(10), 2244-2249.
[NPL 7] Japan J. Pharmacol., 43, pp. 81-90, 1987.
[NPL 8] New Engl. J. Med., 2015, 24, 2522-2533.
[NPL 9] CHEST 2003, 123, 1583-1588.
[NPL 10] Br. Heart J., 53, pp. 173-179, 1985.
[NPL 11] The Lancet, 1, 4880, pt 1, pp. 569-572, 1981.
[NPL 12] Eur. J. Pharmacol., 449, pp. 167-176, 2002.
[NPL 13] The Journal of Clinical Investigation, 117, pp. 464-472, 2007.
[NPL 14] Am. J. Physiol. Lung Cell Mol. Physiol., 296: L648-L656, 2009.

SUMMARY OF INVENTION

Technical Problem

An object of the present invention is to provide a stabilized solid preparation containing Compound (I). Here, the term "stabilized" means that the decrease in the content of Compound (I) contained in the solid preparation due to decomposition thereof is suppressed.

Solution to Problem

As a result of intensive studies for achieving the above object, the present inventors found that the stability of Compound (I) in a solid preparation is improved by using D-mannitol having a specific surface area of 1.0 $m^2/g$ or less as a diluent for Compound (I), and thus completed the present invention.

That is, the present invention is as follows.

(A) A solid preparation containing Compound (I) and D-mannitol having a specific surface area of 1.0 $m^2/g$ or less.

(B) The solid preparation described in (A), wherein the amount of D-mannitol is from 5 to 10000 parts by weight with respect to 1 part by weight of Compound (I).

(C) The solid preparation described in (A) or (B), wherein the content of D-mannitol is from 10 to 99 wt % of the total weight of the solid preparation.

(D) The solid preparation described in any one of (A) to (C), wherein D-mannitol accounts for 20 wt % or more of the total weight of diluents contained in the solid preparation.

(E) The solid preparation described in (A), wherein the content of D-mannitol is (a) such that the weight of D-mannitol is from 5 to 10000 parts by weight with respect to 1 part by weight of Compound (I), (b) from 10 to 99 wt % of the total weight of the solid preparation, and (c) 20% or more of the total weight of diluents contained in the solid preparation.

(F) The solid preparation described in any one of (A) to (E), further comprising a diluent other than D-mannitol and a binder.

(G) The solid preparation described in (F), wherein the diluent other than D-mannitol is one type or two types selected from the group consisting of cornstarch, sucrose, and crystalline cellulose.

(H) The solid preparation described in (F), wherein the binder is hydroxypropyl cellulose.

(I) The solid preparation described in any one of (A) to (E), further containing (a) one type or two types selected from the group consisting of cornstarch, sucrose, and crystalline cellulose, and (b) hydroxypropyl cellulose.

(J) The solid preparation described in (I), wherein (a) the content of Compound (I) is from 0.1 to 2 wt % of the total weight of the solid preparation, (b) the content of D-mannitol is from 20 to 80 wt % of the total weight of the solid preparation, (c) the content of cornstarch is from 15 to 40 wt % of the total weight of the solid preparation, and (d) the content of hydroxypropyl cellulose is from 1 to 5 wt % of the total weight of the solid preparation.

(K) The solid preparation described in (J), wherein Compound (I) is a Form-I crystal.

(L) The solid preparation described in any one of (A) to (K), wherein the solid preparation is a tablet or a granule.

(M) The solid preparation described in any one of (A) to (L), which is used for treating diabetic neuropathy, diabetic gangrene, a peripheral circulatory disturbance, chronic arterial occlusion, intermittent claudication, scleroderma, thrombosis, pulmonary hypertension, myocardial infarction, angina pectoris, glomerulonephritis, diabetic nephropathy, chronic renal failure, bronchial asthma, interstitial pneumonia (pulmonary fibrosis), a chronic obstructive pulmonary disease, tubulointerstitial nephritis, an inflammatory bowel disease, or a symptom associated with spinal canal stenosis.

(N) The solid preparation described in (M), which is used for treating pulmonary hypertension.

(O) The solid preparation described in (M), which is used for treating a peripheral circulatory disturbance.

(P) The solid preparation described in (M), which is used for treating chronic arterial occlusion.

(Q) The solid preparation described in (M), which is used for treating intermittent claudication.

(R) The solid preparation described in (M), which is used for treating a symptom associated with spinal canal stenosis.

(S) The solid preparation described in (M), which is used for treating pulmonary fibrosis.

(T) The solid preparation described in (M), which is used for treating scleroderma.

(U) The solid preparation described in (M), which is used for treating chronic renal failure.

(V) The solid preparation described in (M), which is used for treating tubulointerstitial nephritis.

DESCRIPTION OF EMBODIMENTS (Compound (I))

Compound (I) can be produced in accordance with the method described in, for example, PTL 1 or 2, and the following crystals of three forms are known (PTL 2).

(1) A Form-I crystal of Compound (I), for which a powder X-ray diffraction diagram is obtained using a Cu-Kα radiation (λ=1.54 Å), and which shows diffraction peaks at the following diffraction angles (2θ): 9.4°, 9.8°, 17.2°, and 19.4° in the powder X-ray diffraction spectrum of Compound (I).

(2) A Form-II crystal of Compound (I), for which a powder X-ray diffraction diagram is obtained using a Cu-Kα radiation (λ=1.54 Å), and which shows diffraction peaks at the following diffraction angles (2θ): 9.0°, 12.9°, 20.7°, and 22.6° in the powder X-ray diffraction spectrum of Compound (I).

(3) A Form-III crystal of Compound (I), for which a powder X-ray diffraction diagram is obtained using a Cu-Kα radiation (λ=1.54 Å), and which shows diffraction peaks at the following diffraction angles (2θ): 9.3°, 9.7°, 16.8°, 20.6°, and 23.5° in the powder X-ray diffraction spectrum of Compound (I).

Compound (I) which can be used in the solid preparation of the present invention may be any of the above-mentioned crystals, and further, it may be a mixture of these crystals or may be amorphous. Above all, the Form-I crystal is preferred.

Figure 1:
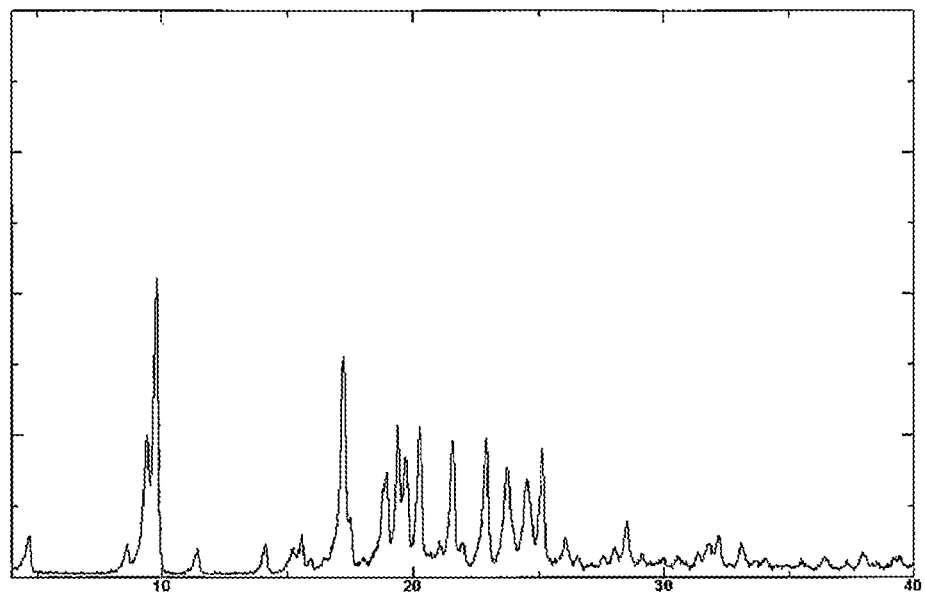
FIG. 1 shows a powder X-ray diffraction spectrum chart of a Form-I crystal of Compound (I). The vertical axis represents a peak intensity (cps) and the horizontal axis represents a diffraction angle (2θ [°]).
Figure 2:
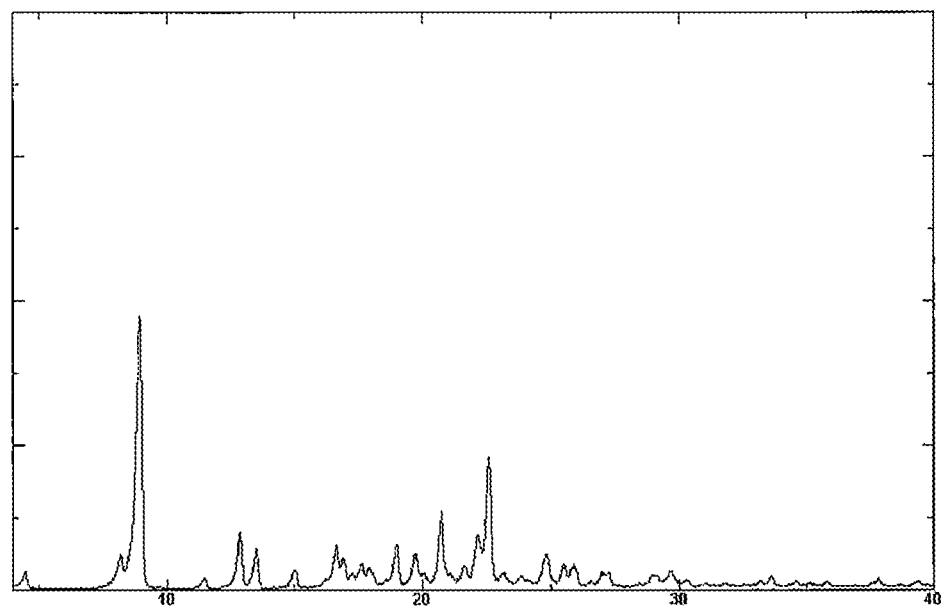
FIG. 2 shows a powder X-ray diffraction spectrum chart of a Form-II crystal of Compound (I). The vertical axis represents a peak intensity (cps) and the horizontal axis represents a diffraction angle (2θ[°]).
Figure 3:
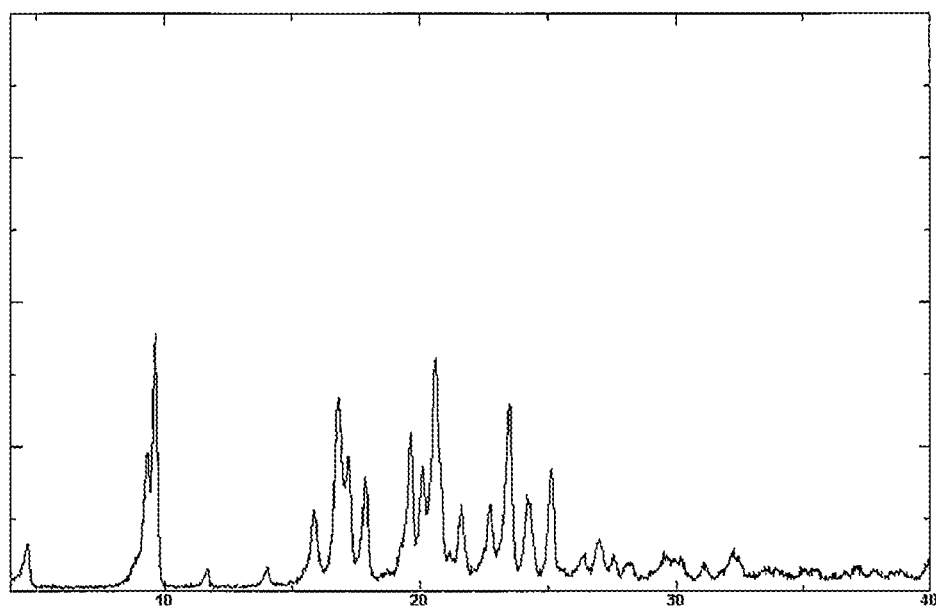
FIG. 3 shows a powder X-ray diffraction spectrum chart of a Form-III crystal of Compound (I). The vertical axis represents a peak intensity (cps) and the horizontal axis represents a diffraction angle (2θ [°]).

The powder X-ray diffraction spectrum charts of the above-mentioned crystals of three forms are shown in FIGS. 1 to 3 for reference.

The powder X-ray diffraction spectra of these crystals were measured using RINT-Ultima III (manufactured by Rigaku Corporation) (target: Cu, voltage: 40 kV, current: 40 mA, scan speed: 4°/min).

The amount of Compound (I) contained in the solid preparation of the present invention is preferably from 0.1 to 12 wt %, more preferably from 0.1 to 2 wt % of the total weight of the solid preparation.

(D-Mannitol)

As a diluent for the solid preparation of the present invention, D-mannitol having a specific surface area of 1.0 $m^2/g$ or less is used. The specific surface area is more preferably 0.7 $m^2/g$ or less, further more preferably larger than 0.2 $m^2/g$ and smaller than 0.7 $m^2/g$.

In the present invention, the specific surface area is a value measured by the BET method, and can be measured using, for example, a specific surface area measuring device Macsorb HM model-1220 (Mountech Co., Ltd.).

As an example of D-mannitol to be used in the present invention, for example, Mannit C (Mitsubishi Shoji Foodtech Co., Ltd., average particle diameter: 20 μm), Mannit P (Mitsubishi Shoji Foodtech Co., Ltd., 50 μm), Mannit S (Mitsubishi Shoji Foodtech Co., Ltd., average particle diameter: 150 μm), Pearlitol 25C (Roquette Pharma, average particle diameter: 25 μm), Pearlitol 50C (Roquette Pharma, average particle diameter: 50 μm), Pearlitol 160C (Roquette Pharma, average particle diameter: 160 μm), Nonpareil 108 (100) (Freund Corporation, average particle diameter: 100 μm), and Nonpareil 108 (200) (Freund Corporation, average particle diameter: 200 μm) can be exemplified. Among these, Mannit P, Mannit S, Pearlitol 50C, and Pearlitol 160C are preferred.

As the diluent for the solid preparation of the present invention, D-mannitol having a specific surface area of 1.0 $m^2$/g or less is used. The D-mannitol may account for 20 wt % or more, and more preferably accounts for 50 wt % or more of the total weight of diluents contained in the solid preparation of the present invention. The diluents may be a mixture of two or more types. As the diluents which can be used other than D-mannitol, cornstarch, crystalline cellulose, sucrose, erythritol, isomalt, and the like can be exemplified, and cornstarch, sucrose, and crystalline cellulose are preferred. Cornstarch is more preferred.

The content of cornstarch is preferably from 0.5 to 45%, more preferably 15 to 40% of the total weight of the solid preparation.

(Solid Preparation)

The solid preparation of the present invention is a solid preparation containing Compound (I) and D-mannitol, and is characterized in that the amount of D-mannitol is from 5 to 10000 parts by weight, preferably from 10 to 9500 parts by weight with respect to 1 part by weight of Compound (I).

The content of D-mannitol in the solid preparation of the present invention is generally from 10 to 99 wt %, and is preferably from 15 to 95 wt %, more preferably from 20 to 80 wt % of the total weight of the solid preparation.

In the present invention, unless otherwise specified, the "solid preparation" refers to a solid preparation in a given form to be orally administered, and includes a conventional tablet, an orally disintegrating tablet, a chewable tablet, a troche tablet, a sublingual tablet, an effervescent tablet, a dispersible tablet, a soluble tablet, a powder, a granule, and a capsule. The solid preparation of the present invention includes a single-layer tablet having a single-layer structure and a multi-layer tablet having a multi-layer structure including two or more layers. The shape of the thus obtained solid preparation is not particularly limited, and can be various shapes such as a circle, an ellipse, a caplet, or a doughnut. In order to control the dissolution property of Compound (I), a sustained release property or an enteric release property may be imparted to the solid preparation of the present invention by a known method. Further, the solid preparation of the present invention may be coated with any of various coating agents or a sugar coating agent by a known method for the purpose of improvement of light stability, improvement of appearance, ensuring of discriminability, release control, or the like. Further, in the solid preparation of the present invention, a pigment may be blended for the purpose of improvement of light stability, ensuring of discriminability, or the like, and also, a taste masking agent and a flavoring agent may be blended for the purpose of improvement of flavor, or the like.

In the solid preparation of the present invention, other than the above-mentioned components, pharmaceutically acceptable carriers (excipients) can be blended as long as the effect of the present invention is not inhibited. These excipients can be blended as appropriate in appropriate amounts as, for example, a binder, a disintegrant, a fluidizing agent, a lubricant, a coating agent, a release control agent, a plasticizer, a coloring agent, a taste masking agent, and a flavoring agent. These excipients can be used alone or two or more types thereof can be used in combination.

As the binder, for example, gelatin, pullulan, hydroxypropyl cellulose, methyl cellulose, polyvinylpyrrolidone, macrogol, gum Arabic, dextran, polyvinyl alcohol, pregelatinized starch, and hypromellose can be exemplified, and hydroxypropyl cellulose, polyvinyl alcohol, and hypromellose are preferred, and hydroxypropyl cellulose is more preferred.

The amount of the binder is preferably from 0.1 to 10 wt %, more preferably from 1 to 8 wt %, further more preferably from 1 to 5 wt % of the total weight of the solid preparation.

The amount of hydroxypropyl cellulose is preferably from 0.1 to 10 wt %, more preferably from 1 to 8 wt %, further more preferably from 1 to 5 wt % of the total weight of the solid preparation.

As the disintegrant, for example, carmellose, carmellose calcium, carmellose sodium, croscarmellose sodium, sodium starch glycolate, crospovidone, a cation exchange resin, partially pregelatinized starch, and low-substituted hydroxypropyl cellulose can be exemplified, and low-substituted hydroxypropyl cellulose is preferred.

The amount of the disintegrant is preferably from 0.1 to 10 wt %, more preferably from 1 to 8 wt % of the total weight of the solid preparation.

The amount of low-substituted hydroxypropyl cellulose is preferably from 0.1 to 10 wt %, more preferably from 1 to 8 wt %, further more preferably from 3 to 7 wt % of the total weight of the solid preparation.

As the fluidizing agent, for example, light anhydrous silicic acid, hydrated silicon dioxide, synthetic aluminum silicate, and magnesium aluminometasilicate can be exemplified.

As the lubricant, for example, stearic acid, magnesium stearate, calcium stearate, sodium stearyl fumarate, talc, waxes, DL-leucine, sodium lauryl sulfate, magnesium lauryl sulfate, macrogol, and light anhydrous silicic acid can be exemplified, and magnesium stearate is preferred.

The amount of the lubricant is preferably from 0.1 to 10 wt %, more preferably from 0.2 to 5 wt % of the total weight of the solid preparation.

The amount of magnesium stearate is preferably from 0.1 to 10 wt %, more preferably from 0.2 to 5 wt %, further more preferably from 0.5 to 3 wt % of the total weight of the solid preparation.

As the coating agent, ethyl cellulose, ethyl acrylate-methyl methacrylate copolymer, methacrylic acid copolymer LD, hypromellose acetate succinate, and the like can be exemplified.

As the release control agent, for example, hydroxypropyl cellulose, an ethylene-vinyl acetate copolymer, and polyethylene oxide can be exemplified.

As the plasticizer, for example, triethyl citrate, propylene glycol, and macrogol can be exemplified, and propylene glycol is preferred.

As the coloring agent, for example, titanium oxide, talc, iron sesquioxide, yellow iron sesquioxide, Food Yellow No. 4, and Food Yellow No. 4 Aluminum Lake can be exemplified, and titanium oxide, iron sesquioxide, yellow iron sesquioxide are preferred.

The content of the coloring agent is preferably less than 0.1 wt % of the total weight of the solid preparation.

As the taste masking agent, for example, fructose, xylitol, glucose, and DL-malic acid can be exemplified.

As the flavoring agent, for example, L-menthol and peppermint can be exemplified.

(Method for Producing Solid Preparation)

The solid preparation of the present invention can be produced by a conventional method in the pharmaceutical field. One example of the production method for the solid preparation will be shown below; however, the present invention is by no means limited to this production method.

The solid preparation of the present invention is produced as follows using a powder of Compound (I) which is the active ingredient.

(1) The powder of Compound (I) is mixed with an excipient such as a diluent, thereby forming a powder, or excipients such as a disintegrant and a binder are added to the resulting mixed powder, and the resulting mixture is granulated by any of various known granulation methods, thereby forming a granule.

(2) The obtained mixed powder or granule is filled into a capsule and formed into a capsule or is compression-molded (tableted) and formed into a tablet, directly or after being mixed with excipients such as a lubricant and a fluidizing agent.

(3) According to need, the surface of the obtained mixed powder, granule, capsule, or tablet is coated with a coating agent or a sugar by a known coating method.

The Compound (I) has an excellent $PGI_2$ receptor agonistic effect and is useful as a preventive agent or a therapeutic agent for a $PGI_2$-related disease, for example, transient ischemic attack (TIA), diabetic neuropathy (see, for example, NPL 1), diabetic gangrene (see, for example, NPL 1), a peripheral circulatory disturbance (for example, chronic arteriosclerosis, chronic arterial occlusion (see, for example, NPL 2), intermittent claudication (see, for example, NPL 3), peripheral embolism, or Raynaud's disease) (see, for example, NPL 4 or NPL 5), a connective tissue disease (for example, systemic lupus erythematosus or scleroderma) (see, for example, PTL 3 or NPL 6), a mixed connective tissue disease, a vasculitic syndrome, reocclusion/restenosis after percutaneous transluminal coronary angioplasty (PTCA), arteriosclerosis, thrombosis (for example, acute-phase cerebral thrombosis or pulmonary embolism) (see, for example, NPL 5 or NPL 7), hypertension, pulmonary hypertension such as pulmonary arterial hypertension or chronic thromboembolic pulmonary hypertension (for example, NPL 8 or NPL 9), an ischemic disease (for example, cerebral infarction or myocardial infarction (see, for example, NPL 10)), angina pectoris (for example, stable angina pectoris or unstable angina pectoris) (see, for example, NPL 11), glomerulonephritis (see, for example, NPL 12), diabetic nephropathy (see, for example, NPL 1), chronic renal failure (see, for example, PTL 4), allergy, bronchial asthma (see, for example, NPL 13), ulcer, pressure ulcer (bedsore), restenosis after coronary intervention such as atherectomy or stent implantation, thrombocytopenia by dialysis, a disease in which fibrogenesis in an organ or a tissue is involved [for example, a renal disease (for example, tubulointerstitial nephritis) (see, for example, PTL 3), a respiratory disease (for example, interstitial pneumonia (pulmonary fibrosis) (see, for example, PTL 3), a chronic obstructive pulmonary disease (see, for example, NPL 14), or the like), a digestive disease (for example, hepatocirrhosis, viral hepatitis, chronic pancreatitis, or scirrhous gastric cancer), a cardiovascular disease (for example, myocardial fibrosis), a bone or articular disease (for example, bone marrow fibrosis or rheumatoid arthritis), a skin disease (for example, postoperative cicatrix, burn cicatrix, keloid, or hypertrophic cicatrix), an obstetric disease (for example, uterine fibroid), a urinary disease (for example, prostatic hypertrophy), other diseases (for example, Alzheimer's disease, sclerosing peritonitis, type I diabetes, or postoperative organ adhesion)], erectile dysfunction (for example, diabetic erectile dysfunction, psychogenic erectile dysfunction, psychotic erectile dysfunction, erectile dysfunction due to chronic renal failure, erectile dysfunction after pelvic operation for resection of the prostate, or vascular erectile dysfunction associated with aging or arteriosclerosis) (see, for example, PTL 7), an inflammatory bowel disease (for example, ulcerative colitis, Crohn's disease, intestinal tuberculosis, ischemic colitis, or intestinal ulcer associated with Behcet disease) (see, for example, PTL 5), gastritis, gastric ulcer, an ischemic eye disease (for example, retinal artery occlusion, retinal vein occlusion, or ischemic optic neuropathy), sudden hearing loss, avascular necrosis of bone, an intestinal damage caused by administration of a non-steroidal anti-inflammatory agent (NSAID) (for example, diclofenac, meloxicam, oxaprozin, nabumetone, indomethacin, ibuprofen, ketoprofen, naproxen, or celecoxib) (there is no particular limitation as long as it is a damage occurring in, for example, the duodenum, small intestine, or large intestine; however, for example, a mucosal damage such as erosion or ulcer occurring in the duodenum, small intestine, or large intestine) (see, for example, PTL 8), or a symptom (for example, paralysis, dullness in sensory perception, pain, numbness, or a decrease in walking ability) associated with spinal canal stenosis (for example, cervical spinal canal stenosis, thoracic spinal canal stenosis, lumbar spinal canal stenosis, coexisting cervical and lumbar spinal stenosis, or sacral spinal stenosis) (see, for example, PTL 6). In addition, the solid preparation of the present invention is also useful as an accelerating agent for gene therapy or angiogenic therapy such as autologous bone marrow transplantation, or an accelerating agent for angiogenesis in peripheral revascularization or angiogenic therapy.

EXAMPLES

Hereinafter, the present invention will be described in more detail with reference to Comparative Examples, Examples, and Test Examples; however, these are not intended to limit the present invention.

As Compound (I) used in the present invention, the above-mentioned Form-I crystal was used.

Unless otherwise stated, the following excipients were used in Examples and Comparative Examples. As cornstarch, Nisshoku Cornstarch W (Nihon Shokuhin Kako Co., Ltd.) was used. As crystalline cellulose, Ceolus PH-101 (Asahi Kasei Chemicals Co., Ltd.) was used. As hydroxypropyl cellulose, HPC-SSL (Nippon Soda Co., Ltd.) was used. As low-substituted hydroxypropyl cellulose, LH-11 (Shin-Etsu Chemical Co., Ltd.) was used. As magnesium stearate, vegetable magnesium stearate (specially manufactured) (Taihei Chemical Industrial Co., Ltd.) was used. As sucrose, T.T.G.H granulated sugar (Toyo Sugar Refining Co., Ltd.) was used. As yellow iron sesquioxide, yellow iron sesquioxide (Kishi Kasei Co., Ltd.) was used. As titanium oxide, Tipaque A-100 (Ishihara Sangyo Kaisha, Ltd.) was used. As propylene glycol, propylene glycol (Asahi Glass Co., Ltd.) was used.

(Example 1) Type of D-Mannitol and Stability (1) Preparation of Tablets

Predetermined amounts of Compound (I), each type of D-mannitol, cornstarch, and low-substituted hydroxypropyl cellulose were placed in a fluidized bed granulation/drying machine (MP-01, Powrex Corporation), and a 5% aqueous hydroxypropyl cellulose solution was sprayed thereon while mixing, whereby granules were prepared. In the obtained granules, a predetermined amount of magnesium stearate was mixed, and the resulting mixture was tableted at 800 kg using a rotary tableting machine (Correct, Kikusui Seisakusho, Ltd.), whereby a tablet (diameter: 7 mm, 120 mg/tablet) was prepared. The types of D-mannitol used in the respective Examples and Comparative Examples are shown in Table 1. The bulk density (g/mL) shown in Table 1 means the ratio of the mass of a powder sample in a state where the powder is not tapped (loosened) to the volume of the powder including the factor of an inter-particle void volume, and it was obtained by weighing 25 g of a sample having passed through a sieve with a mesh size of 1000 μm in advance, placing the sample in a measuring cylinder through a funnel, and measuring the volume at that time, followed by calculation. Further, the tap density (g/mL) shown in Table 1 is a bulk density obtained by mechanically tapping a container in which the powder sample is placed, and specifically, it was obtained by tapping the container until no change in the volume was observed, and measuring the volume at that time, followed by calculation.

The components of each tablet and the contents thereof are as shown in Table 2.

TABLE 1

| Example | Trade name | Manufacturer | Average particle diameter (μm) | Tap density (g/ml) | Bulk density (g/ml) |
| --- | --- | --- | --- | --- | --- |
| Example 1-1 | Mannit P | Mitsubishi Shoji Foodtech Co., Ltd. | 50 | 0.86 | 0.40 |
| Example 1-2 | Pearlitol 25C | Roquette Pharma | 25 | 0.71 | 0.36 |
| Example 1-3 | Pearlitol 50C | Roquette Pharma | 50 | 0.78 | 0.42 |
| Example 1-4 | Pearlitol 160C | Roquette Pharma | 160 | 0.78 | 0.50 |
| Example 1-5 | Nonpareil 108 (100) | Freund Corporation | 100 | 0.83 | 0.64 |
| Comparative Example 1-1 | Pearlitol 100SD | Roquette Pharma | 100 | 0.54 | 0.45 |
| Comparative Example 1-2 | Parteck M200 | Merck Co., Ltd. | 150 | 0.60 | 0.49 |

TABLE 2

| Component Name | Composition (mg/tablet) |
| --- | --- |
| Compound (I) | 0.2 |
| D-mannitol (each type) | 75.4 |
| Cornstarch | 36 |
| Low-substituted hydroxypropyl cellulose | 6 |
| Hydroxypropyl cellulose | 1.2 |
| Magnesium stearate | 1.2 |
| Total | 120 |

(2) Evaluation Method and Results

The obtained tablet was placed in a plastic bottle and stored for 1 month in an uncapped state under open conditions at 40° C./75% RH or under open conditions at 60° C. The related substances of Compound (I) in the tablet were measured before and after the storage using high-performance liquid chromatography, and the increased amount of related substances from the start of the test was evaluated. Incidentally, as the "increased amount of related substances (%)" in the table, the decreased amount (peak area) of Compound (I) contained in the preparation before and after the storage is shown. The results and the specific surface area of each type of D-mannitol used are shown in Table 3. It was shown that the produced amount of the related substances was less than 3% in each of the tablets of Examples 1-1 to 1-5. The specific surface area of D-mannitol used in each of these Examples was 1.0 m$^2$/g or less, and it could be confirmed that in a case where D-mannitol having such physical properties was used, the stability of the preparation is improved.

TABLE 3

| | D-mannitol | Increased amount of related substances (%) 40° C./75% RH | 60° C. | Specific surface area (m$^2$/g) |
| --- | --- | --- | --- | --- |
| Example 1-1 | Mannit P | 1.21 | 1.87 | 0.37 |
| Example 1-2 | Pearlitol 25C | 1.51 | 2.91 | 0.59 |
| Example 1-3 | Pearlitol 50C | 1.63 | 2.92 | 0.42 |
| Example 1-4 | Pearlitol 160C | 1.38 | 2.22 | 0.28 |
| Example 1-5 | Nonpareil 108 (100) | 1.57 | 2.88 | 0.61 |
| Comparative Example 1-1 | Pearlitol 100SD | 2.29 | 3.19 | 1.56 |
| Comparative Example 1-2 | Parteck M200 | 3.06 | 5.01 | 3.32 |

(Example 2) Stability when Blending D-Mannitol and Another Diluent (1) Preparation of Tablet Predetermined amounts of Compound (I), D-mannitol (Mannit P, Mitsubishi Shoji Foodtech Co., Ltd.), cornstarch, and crystalline cellulose were placed in a fluidized bed granulation/drying machine (MP-01, Powrex Corporation), and a 10% aqueous hydroxypropyl cellulose solution was sprayed thereon while mixing, whereby granules were produced. In the obtained granules, predetermined amounts of low-substituted hydroxypropyl cellulose and magnesium stearate were mixed, and the resulting mixture was tableted at 1000 kg using a rotary tableting machine (Correct, Kikusui Seisakusho, Ltd.), whereby a tablet (diameter: 8 mm, 190 mg/tablet) was prepared. The contents of the respective components are as shown in Table 4.

TABLE 4

| | Composition (mg/tablet) | | |
| --- | --- | --- | --- |
| Component Name | Example 2-1 | Example 2-2 | Example 2-3 |
| Compound (I) | 0.2 | 0.2 | 0.2 |
| D-mannitol (Mannit P) | 173.4 | 138.72 | 138.72 |
| Cornstarch | — | 34.68 | — |
| Crystalline cellulose | — | — | 34.68 |

TABLE 4-continued

| | Composition (mg/tablet) | | |
|---|---|---|---|
| Component Name | Example 2-1 | Example 2-2 | Example 2-3 |
| Hydroxypropyl cellulose | 5 | 5 | 5 |
| Low-substituted hydroxypropyl cellulose | 9.5 | 9.5 | 9.5 |
| Magnesium stearate | 1.9 | 1.9 | 1.9 |
| Total | 190 | 190 | 190 |

(2) Evaluation Method and Results

The tablet prepared in (1) was placed in a plastic bottle along with a desiccant (Dryern tablet PW 2010, Yamani Yakuhin Co., Ltd.) and airtightly sealed, and then, stored for 6 months under conditions of 40° C./75% RH (accelerated test). Further, the tablet was placed in a plastic bottle and stored for 1 month in an uncapped state under conditions of 40° C./75% RH or under conditions of 60° C. The content of Compound (I) in the tablet was measured before and after the storage using high-performance liquid chromatography, and the residual ratio of Compound (I) relative to the amount at the start of the test was evaluated.

The results are shown in Table 5. Not only in a case where only D-mannitol was used as the diluent (Example 2-1), but also in a case where cornstarch (Example 2-2) or crystalline cellulose (Example 2-3) was blended along with D-mannitol, a high residual ratio was shown.

TABLE 5

| | Residual ratio of Compound (I) (%) | | |
|---|---|---|---|
| | 40° C./75% RH, airtightly sealed 6 months | 40° C./75% RH, Open 1 month | 60° C., Open 1 month |
| Example 2-1 | 97.8 | 97.4 | 97.5 |
| Example 2-2 | 96.9 | 98.7 | 98.1 |
| Example 2-3 | 97.0 | 98.1 | 97.0 |

(Example 3) Stability of Granule (1) Preparation of Granule

Example 3-1

Predetermined amounts of Compound (I), D-mannitol (Mannit P, Mitsubishi Shoji Foodtech Co., Ltd.), cornstarch, and sucrose (obtained by grinding using a sample mill (AP-S, Hosokawa Micron Corporation, screen diameter: 3 mm)) were placed in a fluidized bed granulation/drying machine (MP-01, Powrex Corporation), and a 10% aqueous hydroxypropyl cellulose solution was sprayed thereon while mixing, whereby a granule was produced.

Example 3-2

Predetermined amounts of Compound (I), D-mannitol (Mannit P, Mitsubishi Shoji Foodtech Co., Ltd.), and cornstarch were placed in a fluidized bed granulation/drying machine (MP-01, Powrex Corporation), and a 10% aqueous hydroxypropyl cellulose solution in which a predetermined amount of yellow iron sesquioxide was dispersed was sprayed thereon while mixing, whereby a granule was produced.

The components of each granule and the contents thereof are as shown in Table 6.

TABLE 6

| | Composition (mg/tablet) | |
|---|---|---|
| Component Name | Example 3-1 | Example 3-2 |
| Compound (I) | 0.1 | 0.1 |
| Cornstarch | 9.9 | 9.9 |
| D-mannitol (Mannit P) | 475 | 950 |
| Sucrose | 475 | — |
| Hydroxypropyl cellulose | 40 | 40 |
| Yellow iron sesquioxide | — | 1 |
| Total | 1000 | 1001 |

(2) Evaluation Method and Results

The obtained granule was placed in a plastic bottle along with a desiccant (Dryern tablet PW 2010, Yamani Yakuhin Co., Ltd.) and hermetically sealed, and then, stored for 2 months under conditions of 40° C./75% RH (acceleration test) or stored for 1 month in an open state. The content of Compound (I) in the granule was measured before and after the storage using high-performance liquid chromatography, and the residual ratio (%) of Compound (I) relative to the amount at the start of the test was evaluated. The results are shown in Table 7. As a result, it was found that high stability is ensured also in a case where it is formulated into a granule.

TABLE 7

| | Residual ratio of Compound (I) (%) | |
|---|---|---|
| | 40° C. 75% RH, airtightly sealed 2 months | 40° C. 75% RH, Open 1 month |
| Example 3-1 | 100.7 | 99.1 |
| Example 3-2 | (not measured) | 98.2 |

INDUSTRIAL APPLICABILITY

According to the present invention, a solid preparation containing stabilized Compound (I), that is, a solid preparation in which the storage stability as a preparation is improved, and the decrease in the content of the active ingredient due to decomposition of the active ingredient and the production and increase of the decomposed products (related substances) of the active ingredient are suppressed can be provided.

The invention claimed is:

1. A solid, preparation comprising:
   2-{4-[N-(5,6-diphenylpyrazin-2-yl)-N-isopropylamino]butyloxy}-N-(methylsulfonyl)acetamide; and
   D-mannitol having a specific surface area of larger than 0.2 m²/g, and 1.0 m²/g or less;
   wherein the content of D-mannitol is:
   (a) such that the weight of D-mannitol is from 5 to 10000 parts by weight with respect to 1 part by weight of 2-{4-[N-(5,6-diphenylpyrazin-2-yl)-N-isopropylamino]butyloxy}-N-(methylsulfonyl)acetamide,
   (b) from 10 to 99 wt % of the total weight of the solid preparation, and
   (c) 20 wt % or more of the total weight of diluents contained in the solid preparation.

2. The solid preparation according to claim 1, further comprising a diluent other than D-mannitol and a binder.

3. The solid preparation according to claim 2, wherein the diluent other than D-mannitol is one type or two types selected from the group consisting of cornstarch, sucrose, and crystalline cellulose.

4. The solid preparation according to claim 2, wherein the binder is hydroxypropyl cellulose.

5. The solid preparation according to claim 1, further comprising:
  (d) one type or two types selected from the group consisting of cornstarch, sucrose, and crystalline cellulose; and
  (e) hydroxypropyl cellulose.

6. The solid preparation according to claim 5, wherein
  (f) the content of 2-{4-[N-(5,6-diphenylpyrazin-2-yl)-N-isopropylamino]butyloxy}-N-(methylsulfonyl)acetamide is from 0.1 to 2 wt % of the total weight of the solid preparation,
  (b) the content of D-mannitol is from 20 to 80 wt % of the total weight of the solid preparation,
  (g) the content of cornstarch is from 15 to 40 wt % of the total weight of the solid preparation, and
  (h) the content of hydroxypropyl cellulose is from 1 to 5 wt % of the total weight c f the solid preparation.

7. The solid preparation according to claim 1, wherein 2-{4-[N-5,6-diphenylpyrazin-2-yl)-N-isopropylamino]butyloxy}-N-(methylsulfonyl)acetamide is a Form-I crystal.

8. The solid preparation according to claim 1, wherein the solid preparation is a tablet or a granule.

9. A method for treating diabetic neuropathy, diabetic gangrene, a peripheral circulatory disturbance, chronic arterial occlusion, intermittent claudication, scleroderma, thrombosis, pulmonary hypertension, myocardial infarction, angina pectoris, glomerulonephritis, diabetic nephropathy, chronic renal failure, bronchial asthma, interstitial pneumonia, a chronic obstructive pulmonary disease, tubulointerstitial nephritis, an inflammatory bowel disease, or a symptom associated with spinal canal stenosis, the method comprising the step of administering to a subject, a solid preparation comprising:
  2-{4-[N-(5,6-diphenylpyrazin-2-yl)-N-isopropylamino]butyloxy}-N-(methylsulfonyl)acetamide; and
  D-mannitol having a specific surface area of larger than 0.2 m²/g, and 1.0 m²/g or less;
wherein the content of D-mannitol is:
  (a) such that the weight of D-mannitol is from 5 to 10000 parts by weight with respect 1 part by weight of 2-{4-[N-(5,6-diphenylpyrazin-2-yl)-N-isopropylamino]butyloxy}-N-(methylsulfonyl)acetamide,
  (b) from 10 to 99 wt % of the total weight of the solid preparation, and
  (c) 20 wt % or more of the total weight of diluents contained in the solid preparation.

10. The method according to claim 9, wherein what is treated is pulmonary hypertension.

11. The method according to claim 9, wherein what is treated is a peripheral circulatory disturbance.

12. The method according to claim 9, wherein what is treated is chronic arterial occlusion.

13. The method according to claim 9, wherein what is treated is intermittent claudication.

14. The method according to claim 9, wherein what is treated is a symptom associated with spinal canal stenosis.

15. The method according to claim 9, wherein what is treated is interstitial pneumonia and the interstitial pneumonia treated is pulmonary fibrosis.

16. The method according to claim 9, wherein what is treated is scleroderma.

17. The method according to claim 9, wherein what is treated is chronic renal failure.

18. The method according to claim 9, wherein what is treated is tubulointerstitial nephritis.

19. The method according to claim 10, wherein the pulmonary hypertension treated is pulmonary arterial hypertension.

20. The method according to claim 19, wherein the solid preparation further comprises a diluent other than D-mannitol and a binder.

21. The method according to claim 19, wherein the solid preparation further comprises:
  (d) one type or two types selected from the group consisting of cornstarch, sucrose, and crystalline cellulose; and
  (e) hydroxypropyl cellulose.

22. The method according to claim 21, wherein the solid preparation comprises cornstarch, and
  (f) the content of 2-{4-[N-(5,6-diphenylpyrazin-2-yl)-N-isopropylamino]butyloxy}-N-(methylsulfonyl)acetamide is from 0.1 to 2 wt % of the total weight of the solid preparation,
  (b) the content of D-mannitol is from 20 to 80 wt % of the total weight of the solid preparation,
  (g) the content of cornstarch is from 15 to 40 wt % of the total weight of the solid preparation, and
  (h) the content of hydroxypropyl cellulose is from 1 to 5 wt % of the total weight of the solid preparation.

23. The method according to claim 19, wherein the solid preparation is a tablet.

24. The method according to claim 23, wherein D-mannitol has a specific surface area of larger than 0.2 m²/g and smaller than 0.7 m²/g, and the content of D-mannitol is:
  (a) such that the weight of D-mannitol is from 10 to 9500 parts by weight with respect to 1 part by weight of 2-{4-[N-(5,6-diphenylpyrazin-2-yl)-N-isopropylamino]butyloxy}-N-(methylsulfonyl)acetamide,
  (b) from 20 to 80 wt % of the total weight of the solid preparation, and
  (c) 50 wt % or more of the total weight of diluents contained in the solid preparation.

25. The method according to claim 24, wherein the solid preparation further comprises:
  (d) one type or two types selected from the group consisting of cornstarch, sucrose, and crystalline cellulose; and
  (e) hydroxypropyl cellulose.

26. The method according to claim 25, wherein the solid preparation comprises cornstarch, and
  (f) the content of 2-{4-[N-(5,6-diphenylpyrazin-2-yl)-N-isopropylamino]butyloxy}-N-(methylsulfonyl)acetamide is from 0.1 to 2 wt % of the total weight of the solid preparation,
  (g) the content of cornstarch is from 1.5 to 40 wt % of the total weight of the solid preparation, and
  (h) the content of hydroxypropyl cellulose is from 1 to 5 wt % of the total weight of the solid preparation.

* * * * *